United States Patent
Gan et al.

(10) Patent No.: US 11,808,765 B2
(45) Date of Patent: Nov. 7, 2023

(54) METHOD AND DEVICE FOR DETECTING EXCESSIVE ANTIGEN CONCENTRATION AND STORAGE MEDIUM

(71) Applicant: EDAN INSTRUMENTS, INC., Guangdong (CN)

(72) Inventors: Quan Gan, Guangdong (CN); Lifeng Zhao, Guangdong (CN); Yawen Han, Guangdong (CN)

(73) Assignee: EDAN INSTRUMENTS, INC., Shenzhen (CN)

(*) Notice: Subject to any disclaimer, the term of this patent is extended or adjusted under 35 U.S.C. 154(b) by 826 days.

(21) Appl. No.: 16/437,714

(22) Filed: Jun. 11, 2019

(65) Prior Publication Data

US 2019/0383810 A1 Dec. 19, 2019

(30) Foreign Application Priority Data

Jun. 14, 2018 (CN) .......................... 201810615214.8

(51) Int. Cl.
*G01N 33/566* (2006.01)
*G01N 33/536* (2006.01)
*G01N 33/487* (2006.01)
*G01N 33/532* (2006.01)

(52) U.S. Cl.
CPC ..... *G01N 33/566* (2013.01); *G01N 33/48707* (2013.01); *G01N 33/48785* (2013.01); *G01N 33/532* (2013.01); *G01N 33/536* (2013.01)

(58) Field of Classification Search
CPC ........... G01N 33/566; G01N 33/48785; G01N 33/532; G01N 33/536
See application file for complete search history.

(56) References Cited

U.S. PATENT DOCUMENTS 6,743,581 B1* 6/2004 Vo-Dinh .......... G01N 33/54373
435/174
2015/0065372 A1* 3/2015 Amir .................. G01N 33/6893
435/6.12

* cited by examiner

*Primary Examiner* — Gailene Gabel
(74) *Attorney, Agent, or Firm* — Amanda M. Prose; Westman, Champlin & Koehler, P.A.

(57) ABSTRACT

Provided are a method and device for detecting an excessive antigen concentration, and a storage medium. The method includes: subjecting a sample containing antigens to an immune reaction, obtaining a photovoltage value of the sample after subjected to the immune reaction; and determining whether an antigen concentration of the sample is excessive according to the photovoltage value of the sample.

9 Claims, 3 Drawing Sheets

METHOD AND DEVICE FOR DETECTING EXCESSIVE ANTIGEN CONCENTRATION AND STORAGE MEDIUM

CROSS-REFERENCE TO RELATED APPLICATION

This application claims priority to and benefits of Chinese Patent Application Serial No. 201810615214.8, filed with the State Intellectual Property Office of P. R. China on Jun. 14, 2018, the entire content of which is incorporated herein by reference.

FIELD

The present disclosure relates to the field of clinical testing technology, and more particularly to a method and device for detecting an excessive antigen concentration, and a storage medium.

BACKGROUND

Human C-reactive proteins (CRPs) are such proteins (acute proteins) that sharply rise in plasma when a body is infected or a tissue is damaged. CRP concentration will increase dramatically in blood during acute trauma or infection, and thus is the most commonly used indicator of an acute phase reaction in clinic. Therefore, the accurate measurement of the CRP concentration in the blood is of great value. However, due to various limitations, existing test conditions are not sufficient to measure samples in some CRP concentration ranges, especially samples with high CRP concentrations.

In the related art, a sample with excessive antigens may be measured after being diluted in vitro at a higher dilution ratio, which, however, is unable to achieve fully automatic detection of the excessive antigen concentration. Alternatively, the sample with excessive antigens may be measured in a pre-reaction way, wherein each sample need to be added with additional antigens, and then detected whether a new rate peak occurs during the new immune reaction. When the antigen concentration is excessive, the new rate peak will not occur after the additional antigens are added, in such a case, an instrument will dilute the sample and measure the antigen concentration thereof. With the pre-reaction way, the reagent consumption is increased, the cost for single sample measurement is higher, the process control is complicated, the measurement is restricted by a reaction rule of the reagent itself, and the instrument is required to have a higher sensitivity.

SUMMARY

Embodiments of the present disclosure seek to solve at least one of the problems existing in the related art to at least some extent.

Embodiments of a first aspect of the present disclosure provide a method for detecting an excessive antigen concentration, including: subjecting a sample containing antigens to an immune reaction, and obtaining a photovoltage value of the sample after subjected to the immune reaction; and determining whether an antigen concentration of the sample is excessive according to the photovoltage value of the sample.

Embodiments of a second aspect of the present disclosure provide an apparatus for detecting an excessive antigen concentration, including: a reaction module configured to subject a sample containing antigens to an immune reaction; a photoelectric module configured to obtain a photovoltage value of the sample after subjected to the immune reaction; and a calculating module configured to determine whether an antigen concentration of the sample is excessive according to the photovoltage value of the sample.

Embodiments of a third aspect of the present disclosure provide a non-transitory computer-readable storage medium having stored therein instructions that, when executed by a processor of a mobile terminal, cause the mobile terminal to perform a method for detecting an excessive antigen concentration, the method including: subjecting a sample containing antigens to an immune reaction, and obtaining a photovoltage value of the sample after subjected to the immune reaction; and determining whether an antigen concentration of the sample is excessive according to the photovoltage value of the sample.

Embodiments of a fourth aspect of the present disclosure provide a computer program product having stored therein instructions that, when executed by a processor, cause the processor to perform a method for detecting an excessive antigen concentration, the method including: subjecting a sample containing antigens to an immune reaction, and obtaining a photovoltage value of the sample after subjected to the immune reaction; and determining whether an antigen concentration of the sample is excessive according to the photovoltage value of the sample.

Embodiments of a fifth aspect of the present disclosure provide a device for detecting an excessive antigen concentration, including: a processor; and a memory for storing instructions executable by the processor; wherein the processor is configured to perform a method for detecting an excessive antigen concentration as described above.

Additional aspects and advantages of embodiments of the present disclosure will be provided in part in the following descriptions, become apparent in part from the following descriptions, or be learned from the practice of the embodiments of the present disclosure.

BRIEF DESCRIPTION OF THE DRAWINGS

These and other aspects and advantages of embodiments of the present disclosure will become apparent and more readily appreciated from the following descriptions made with reference to the drawings, in which.

DETAILED DESCRIPTION

Figure 1:
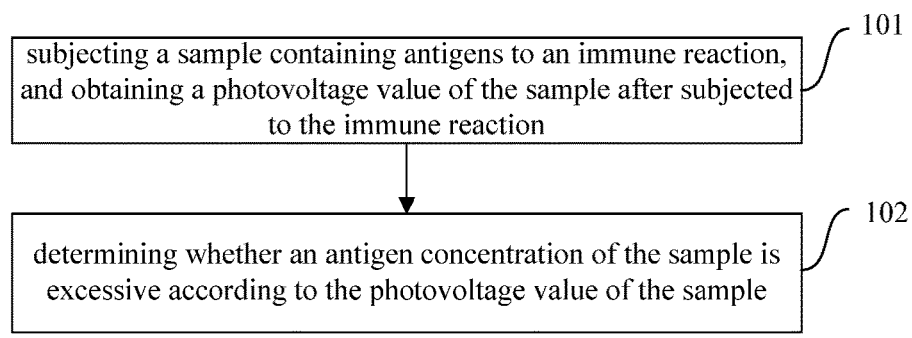
FIG. 1 is a flow chart of a method for detecting an excessive antigen concentration according to an embodiment of the present disclosure.

Embodiments of the present disclosure will be described in detail below, examples of which are shown in the accompanying drawings, in which the same or similar elements and elements having same or similar functions are denoted by like reference numerals throughout the descriptions. Embodiments described herein with reference to the accompanying drawings are explanatory and illustrative, which are used to generally understand the present disclosure, and shall not be construed to limit the present disclosure. Instead, the embodiments of the present disclosure include all the variants, modifications and their equivalents within the spirit and scope of the appended claims.

FIG. 1 is a flow chart of a method for detecting an excessive antigen concentration according to an embodiment of the present disclosure.

The present embodiment is illustrated by an example in which the method for detecting an excessive antigen concentration is configured in an apparatus for detecting an excessive antigen concentration.

In the present embodiment, the method for detecting the excessive antigen concentration may be configured in the apparatus for detecting the excessive antigen concentration, and the apparatus for detecting the excessive antigen concentration may be disposed in a server or an electronic device, which will not be specifically limited herein.

The present embodiment is illustrated by an example in which the method for detecting the excessive antigen concentration is configured in the electronic device.

Embodiments of the present disclosure are illustrated by taking the detection of the excessive antigen concentration for a CRP sample as an example. However, it will be appreciated that, the present disclosure is not limited thereto.

The electronic device, such as a smart phone, a tablet computer, a personal digital assistant, an e-book, etc., has hardware parts of various operating systems.

It should be noted that, an executive body of embodiments of the present disclosure may be, for example, a central processing unit (CPU) of the electronic device in hardware, or may be, for example, an application for detecting an excessive antigen concentration of the electronic device in software, which will not be specifically limited herein.

CRPs are such proteins (acute proteins) that sharply rise in plasma when a body is infected or a tissue is damaged. CRP concentration will increase dramatically in blood during acute trauma or infection, and thus is the most commonly used indicator of an acute phase reaction in clinic. Therefore, the accurate measurement of the CRP concentration in the blood is of great value. However, due to various limitations, existing test conditions are not sufficient to measure samples in some CRP concentration ranges, especially samples with high CRP concentrations.

In the related art, a sample with excessive antigens may be measured after diluted in vitro at a higher dilution ratio, which, however, is unable to achieve fully automatic detection of the excessive antigen concentration. Alternatively, the sample with excessive antigens may be measured in a pre-reaction way, wherein each sample need to be added with additional antigens, and then detected whether a new rate peak occurs during the new immune reaction. When the antigen concentration is excessive, the new rate peak will not occur after the additional antigens are added, in such a case, an instrument will dilute the sample and measure the antigen concentration thereof. With the pre-reaction way, the reagent consumption is increased, the cost for single sample measurement is higher, the process control is complicated, the measurement is restricted by a reaction rule of the reagent itself, and the instrument is required to have a higher sensitivity.

In order to solve at least one of the above technical problems to at least some extent, embodiments of the present disclosure provide a method for detecting an excessive antigen concentration, by subjecting a sample containing antigens to an immune reaction, and obtaining a photovoltage value of the sample after subjected to the immune reaction; and determining whether an antigen concentration of the sample is excessive according to the photovoltage value of the sample, the automatic detection of the excessive antigen concentration is realized. Moreover, as the detection is based on respective photovoltage values of individual samples, the detection process is effective and relatively simple, thereby effectively saving the detection cost, and improving the detection effect of the excessive antigen concentration.

As illustrated in FIG. 1, the method includes the following operations as illustrated at blocks of FIG. 1.

At block 101, a sample containing antigens is subjected to an immune reaction, and a photovoltage value of the sample after subjected to the immune reaction is obtained.

Embodiments of the present disclosure are illustrated taking the detection of the excessive antigen concentration for a CRP sample as an example. However, it will be appreciated that, the present disclosure is not limited thereto.

In an implementation of embodiments of the present disclosure, the CRP sample containing antigens may be subjected to the immune reaction first. For example, the CRP sample is added into a dilution cuvette by a sampling needle to obtain a diluted sample, and the diluted solution is transferred into a reaction cuvette by a reagent needle to undergo the immune reaction, triggering the detection of the excessive antigen concentration.

Afterwards, in the detection process of the excessive antigen concentration, the photovoltage value of the sample after subjected to the immune reaction is obtained.

In embodiments of the present disclosure, the photovoltage value of the sample may be obtained at a plurality of consecutive preset time points after the immune reaction so as to continuously determine whether the antigen concentration of the sample is excessive.

An example is as follows.

1. In the detection of the excessive antigen concentration, the sampling needle successively moves through rotation and vertical movements to a diluent to take a certain amount of the diluent and moves to a site of sample immune reaction to take the sample, and then adds the diluent and the sample to the dilution cuvette to mix them evenly to obtain a diluted sample.

2. In the process of continuously sampling the diluted sample to the dilution cuvette, a reaction disc continuously rotates to bring the diluted sample to a position where the reagent needle is able to suck back the diluted sample. The next position of the dilution cuvette is reserved for the reaction cuvette, that is, the dilution cuvettes and the reaction cuvettes are alternately arranged.

3. When the diluted sample is rotated to the position where the reagent needle is able to suck the diluted sample, the reagent needle successively moves through the rotation and vertical movements to a buffer site to take the buffer, moves to an antibody site to take the antibody, and then moves to the dilution cuvette to take the diluted sample. The reaction disc rotates to bring the reaction cuvette next to the dilution cuvette to below the reagent needle, and then the mixture in the reagent needle is added to the reaction cuvette and evenly mixed. The reaction cuvette is rotated by the reaction disc to an optical site to obtain optical data. Afterwards, the optical data is processed and analyzed to obtain a photovoltage value of the sample at a certain time point in the reaction process. During the continuous rotation of the reaction disc, the photovoltage values of the sample in the reaction cuvette at different time points are uploaded by optical detection.

4. When multiple samples are continuously tested, the diluted samples are continuously added to the dilution cuvettes by the sampling needles, the reaction solutions are continuously added to the reaction cuvettes by the reagent needles, and the photovoltage values of each reaction cuvette at different time points are continuously read with the continuous rotation of the reaction disc.

In a specific implementation of embodiments of the present disclosure, as the photovoltage values at different time points are obtained for the sample in each reaction cuvette, in order to make the detection results more accurate, the photovoltage values at multiple time points can be utilized to detect the excessive antigen concentration. For example, the photovoltage values obtained at two preset time points may be subjected to a subtraction processing to obtain a photovoltage difference value, and the photovoltage difference value is taken as the photovoltage value of the sample after subjected to the immune reaction. However, it should be illustrated that, the present disclosure is not limited thereto.

Similarly, the photovoltage value as described in the following embodiments may also be understood as the photovoltage difference value.

At block 102, it is determined whether an antigen concentration of the sample is excessive according to the photovoltage value of the sample.

Figure 2:
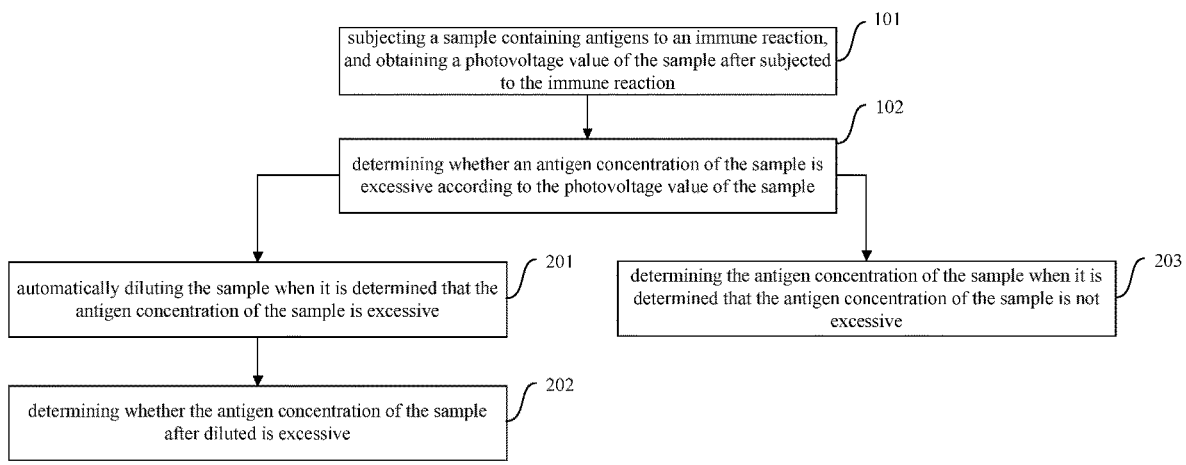
FIG. 2 is a flow chart of a method for detecting an excessive antigen concentration according to an embodiment of the present disclosure.

In embodiments of the present disclosure, in order to ensure that the detection of a sample whose antigen concentration is not excessive is not affected by the detection of a sample with an excessive antigen concentration, so as to make the measurement process more efficient and completely realize the automatic measurement, the following operations as illustrated at blocks shown in FIG. 2 may be operated.

At block 201, the sample is automatically diluted when it is determined that the antigen concentration of the sample is excessive.

At block 202, it is determined whether the antigen concentration of the sample after diluted is excessive.

At block 203, the antigen concentration of the sample is determined when it is determined that the antigen concentration of the sample is not excessive.

In a specific implementation of embodiments of the present disclosure, for ease of understanding, the sample with the excessive antigen concentration is recorded as a first sample, and the sample whose antigen concentration is not excessive is recorded as a second sample.

In a specific implementation of embodiments of the present disclosure, the first sample may be automatically diluted using a preset method. For example, the first sample may be automatically diluted by a predetermined dilution factor, and details may refer to the following embodiments.

In embodiments of the present disclosure, the antigen concentration of the first sample after automatically diluted by the predetermined dilution factor may be not excessive. If the antigen concentration of the first sample after automatically diluted by the predetermined dilution factor is still excessive, dilution of the first sample by the predetermined dilution factor may be performed repeatedly until it is detected that the antigen concentration is not excessive. By setting the above cyclic detection operation, the automatic detection process of the excessive antigen concentration is more complete.

In embodiments of the present disclosure, determining whether the antigen concentration of the sample is excessive according to the photovoltage value of the sample may include: determining an initial concentration value of the sample according to the photovoltage value of the sample; comparing the initial concentration value of the sample with a concentration threshold; determining that the antigen concentration of the sample is excessive when the initial concentration value of the sample is greater than or equal to the concentration threshold; and determining that the antigen concentration of the sample is not excessive when the initial concentration value of the sample is less than the concentration threshold.

Using the above operations, those whose initial concentration values are greater than or equal to the concentration threshold may be determined from a plurality of samples as samples with excessive antigen concentrations. In the subsequent operations, only these samples with the excessive antigen concentrations are diluted for the detection of the antigen concentration, thereby effectively saving the dilution reagent and reducing the cost for detecting the excessive antigen concentration.

In the implementation of determining the initial concentration value of the sample according to the photovoltage value of the sample, a concentration value corresponding to the photovoltage value of the sample may be determined from a predetermined curve as the initial concentration value of the sample.

Figure 3:
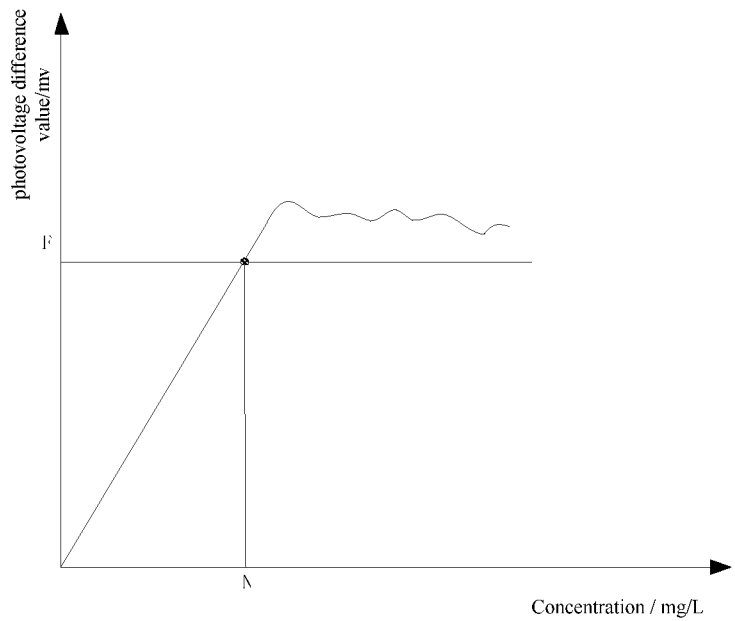
FIG. 3 is a schematic diagram of a predetermined curve according to an embodiment of the present disclosure.

The predetermined curve may be determined according to correspondences between the antigen concentrations and the photovoltage values of a plurality of reference samples, and configured to identify a relation between antigen concentrations and photovoltage values. FIG. 3 is a schematic diagram of a predetermined curve according to an embodiment of the present disclosure, as illustrated in FIG. 3, the horizontal coordinate indicates the concentration, such as the CRP concentration, and the vertical coordinate indicates the photovoltage value.

In some embodiments of the present disclosure, the predetermined curve is pre-generated. Specifically, the predetermined curve may be set by an inspector according to detection experiences, or may be a factory default setting of a device for detecting the excessive antigen concentration, which will not be specifically limited herein.

In embodiments of the present disclosure, when an antigen concentration of an unknown sample is detected, photovoltage values of the unknown sample at different time points are obtained, referring to operations as illustrated at block 101, and a photovoltage difference value (may be used as the photovoltage value of the unknown sample) between two preset time points is calculated and then substituted into a functional relationship $C_{CRP}=f(\Delta U)$ of the predetermined curve to calculate an initial concentration value of the unknown sample.

After the initial concentration value of the unknown sample is determined, the initial concentration value of the sample may be compared with the concentration threshold. When the initial concentration value of the sample is greater than or equal to the concentration threshold, it is determined that the antigen concentration of the sample is excessive. When the initial concentration value of the sample is less than the concentration threshold, it is determined that the antigen concentration of the sample is not excessive.

In a specific implementation of embodiments of the present disclosure, the concentration threshold may be determined based on the above predetermined curve. For example, the concentration threshold is determined by means of statistical analysis of a plurality of reference samples with known antigen concentrations. In the method for detecting the excessive antigen concentration according to embodiments of the present disclosure, the excessive antigen concentration of the unknown sample is detected based on the known antigen concentrations and the corresponding photovoltage values of the reference samples, which makes the detection result more consistent with actual concentration distribution of the samples and improves the detection accuracy.

Figure 4:
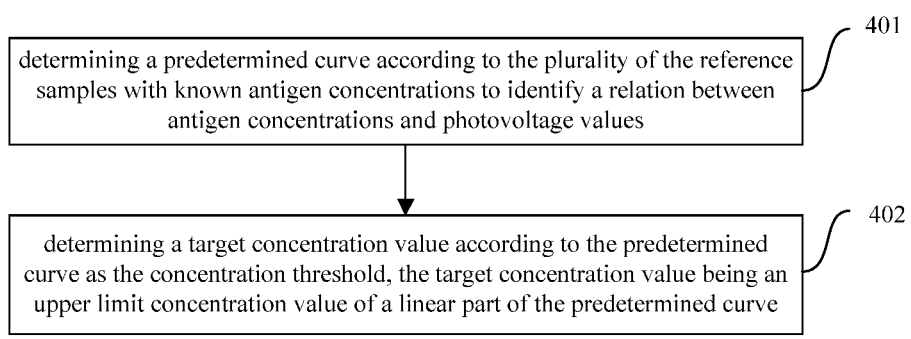
FIG. 4 is a flow chart of a method for detecting an excessive antigen concentration according to an embodiment of the present disclosure.

As illustrated in FIG. 4, the method for determining the concentration threshold may include operations illustrated at the following blocks.

At block 401, a predetermined curve is determined according to the plurality of the reference samples with known antigen concentrations to identify a relation between antigen concentrations and photovoltage values.

The functional relationship $C_{CRP}=f(\Delta U)$ between the CRP concentration ($C_{CRP}$) and the photovoltage value ($\Delta U$) is established based on calibrated measurements of the plurality of the reference samples. During the calibrated measurements, the reference samples with known but different concentrations are tested in accordance with the test process as illustrated at block 101 to obtain the photovoltage difference value of each reference sample after subjected to the immune reaction as the photovoltage value thereof, based on the respective CRP concentrations and the corresponding photovoltage values of the reference samples, the functional relationship between the CRP concentration and the photovoltage value is established, and all the calibrated concentrations and their respective photovoltage values are distributed as coordinate points in the coordinate system. These coordinate points may also be fitted by the principle of a least squares method to obtain the predetermined curve and its functional expression $C_{CRP}=f(\Delta U)$.

At block 402, a target concentration value is determined according to the predetermined curve as the concentration threshold. The target concentration value is an upper limit concentration value of a linear part of the predetermined curve.

According to an immune reaction mechanism of the CRP sample, the reaction of antibodies with antigens will generate conjugates. When the amount of antibodies added to the reaction cuvette is constant, with the continuous increase of the amount of the antigens, the photovoltage value of the sample will not always linearly increase with the concentration value of the antigens, but present a slowly nonlinear increase, and will fluctuate when the antigens reach a certain amount (referring to FIG. 3). In this fluctuating region, the same photovoltage value will correspond to a plurality of concentration values, the photovoltage values at different concentration values are relatively unstable, and the sample with high concentration value cannot be distinguished by the photoelectric value.

In embodiments of the present disclosure, in order to solve the above technical problems, an upper limit of a linear part of the relationship between the photovoltage value and the concentration value may be selected as the concentration threshold, that is, when the concentration value is less than this upper limit, the concentration value and the photovoltage value present a linear relationship, i.e., a one-to-one corresponding relationship, when the concentration value is greater than this upper limit, the concentration value and the photovoltage value present a nonlinear relationship. In embodiments of the present disclosure, the upper limit concentration value of the linear part of the predetermined curve may be determined as the concentration threshold.

In embodiments of the present disclosure, besides using the concentration threshold as the determining condition, the photovoltage value of the sample may be directly compared with a photovoltage threshold to determine whether the antigen concentration of the sample is excessive.

In embodiments of the present disclosure, the photovoltage threshold may be a photovoltage value corresponding to the concentration threshold in the predetermined curve as illustrated in FIG. 3.

In a specific implementation of embodiments of the present disclosure, the concentration threshold or the photovoltage threshold may be adjusted as required, thereby ensuring the flexibility of the application of the method.

In embodiments of the present disclosure, by subjecting the sample containing antigens to the immune reaction, obtaining the photovoltage value of the sample after subjected to the immune reaction; and determining whether the antigen concentration of the sample is excessive according to the photovoltage value of the sample, the automatic detection of the excessive antigen concentration is realized. Moreover, as the detection is based on respective photovoltage values of individual samples, the detection process is effective and relatively simple, thereby effectively saving the detection cost, and improving the detection effect of the excessive antigen concentration.

Figure 5:
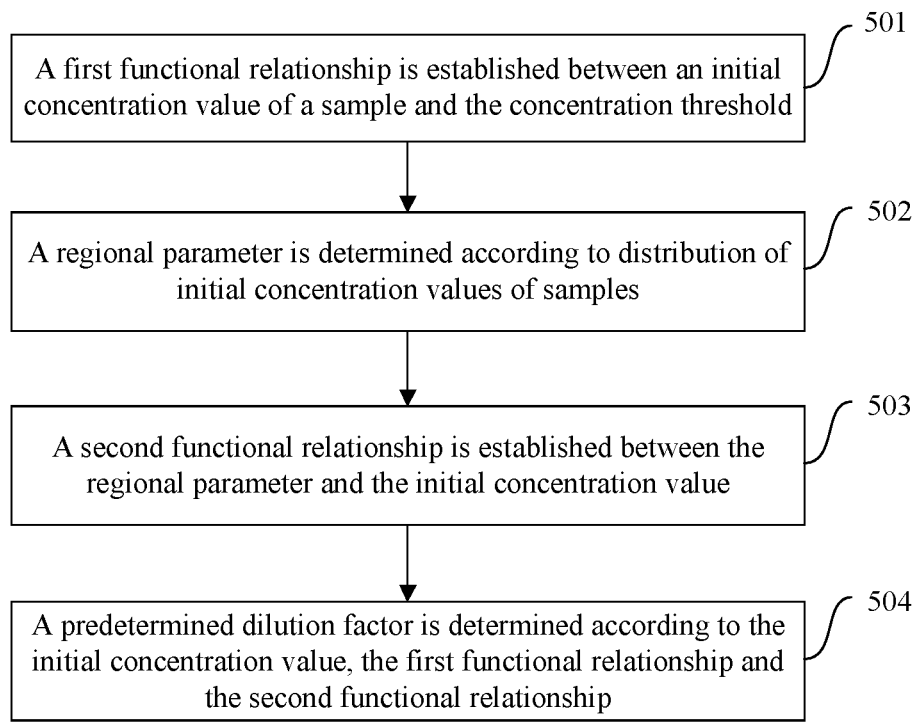
FIG. 5 is a flow chart of a method for detecting an excessive antigen concentration according to an embodiment of the present disclosure.

FIG. 5 is a flow chart of a method for detecting an excessive antigen concentration according to an embodiment of the present disclosure.

In embodiments of the present disclosure, the predetermined dilution factor may be determined in a first manner, and the first manner is a preset algorithm, which may be illustrated with the following example.

As illustrated in FIG. 5, the method includes operation as described at the following blocks.

At block 501, a first functional relationship is established between an initial concentration value of a sample and the concentration threshold.

At block 502, a regional parameter is determined according to distribution of initial concentration values of samples.

At block 503, a second functional relationship is established between the regional parameter and the initial concentration value.

At block 504, the predetermined dilution factor is determined according to the initial concentration value, the first functional relationship and the second functional relationship.

In embodiments of the present disclosure, as an example, the concentration threshold is represented by M, an initial concentration value determined for an unknown sample is represented by N, and the regional parameter is represented by L. First, the first functional relationship $N>f(M)$ may be established between initial concentration values of individual samples and the concentration threshold, and then the predetermined dilution factor S is automatically calculated according to the first functional relationship $N>f(M)$, where the predetermined dilution factor S, the concentration threshold M and the regional parameter L meet a functional relationship of $S=f(M,L)$.

In embodiments of the present disclosure, the regional parameter may be determined according to the distribution of the initial concentration values of individual samples. For example, the distribution of CRP concentrations of samples in a certain range or region is collected based on 4G network or other measured data, the concentration threshold M is determined according to a preferred percentage of the distribution of the CRP concentrations of samples, and then the regional parameter L is determined according to the distribution of initial CRP concentration values N of samples. For example, when a percentage of samples with the initial CRP concentration value N in a range of 0 mg/L to a mg/L is 95%, L is L1; when a percentage of samples with the initial CRP concentration value N in a range of 0 mg/L to b mg/L is 95%, L is L2, and so on, thereby establishing the second functional relationship between the initial concentration value N and the regional parameter L. By combining the second functional relationship with the concentration threshold M and the regional parameter L, a relationship S=f(M,L) among the predetermined dilution factor S with the concentration threshold M and the regional parameter L is obtained.

As another example, the predetermined dilution factor may be determined in a second manner, which is based on an empirical value. Specifically, according to detection experiences, there is an empirical range corresponding to the initial concentration value N of the sample. In embodiments of the present disclosure, an empirical value of the predetermined dilution factor S may be set according to the empirical range. For example, it is assumed that an initial concentration value of a sample is 1000 mg/L, and the concentration threshold is 320 mg/L. In an initial detection of the antigen concentration, it is detected that the initial concentration value of the sample is greater than the concentration threshold, then the dilution of the sample is triggered, for example, the sampling needle may be used to dilute the sample in the dilution cuvette by 2.5 times to obtain a diluted solution with an antigen concentration of 400 mg/L, which is detected to be still greater than the concentration threshold of 320 mg/L, then further dilution of the sample is triggered to obtain a diluted solution with an antigen concentration of 160 mg/L, which is detected to be less than the concentration threshold of 320 mg/L, by then the detection of the antigen concentration of the sample is completed. The detected CRP concentration value is a product of the finally detected concentration value and the total dilution times.

By determining the predetermined dilution factor based on the empirical value, the detection result is more consistent with the actual CRP concentration distribution of samples, so that the detection result is more accurate.

In a specific implementation of embodiments of the present disclosure, a target manner may be determined from the first manner and the second manner according to a parameter related to detection environment, and the predetermined dilution factor is determined in the target manner. The parameter includes: a test department identification, a test area identification, sample distribution, and concentration distribution of samples of the detection environment.

By selecting an appropriate manner according to the parameter related to the detection environment to determine the predetermined dilution factor, the accuracy of the detection result is guaranteed from another dimension due to the comprehensive consideration of some parameters related to the detection environment.

In a specific implementation of embodiments of the present disclosure, the detection of the excessive antigen concentration may be automatically called when a plurality of samples are continuously detected.

In embodiments of the present disclosure, the above process of determining the CRP concentration of the first sample may be referred to as a first antigen concentration detection, the above process of determining the CRP concentration of the second sample may be referred to as a second antigen concentration detection, and the first and second antigen concentration detections are parallel detection processes. During the parallel detection processes, it is continually detected whether the antigen concentration is excessive according to the concentration threshold or the photovoltage threshold, and then it is continually switched to call the first antigen concentration detection or the second antigen concentration detection, which is capable of achieving the compatibility of the first and second antigen concentration detections, improving the detection efficiency of the antigen concentration, and timely triggering the subsequent dilution operation when it is detected that the antigen concentration is excessive.

As an example, antigen concentrations of four samples A, B, C, and D are detected in sequence, and concentration values of each sample detected in subsequent continuous detections are within the concentration threshold. It is assumed that initial concentration values of the four samples A, B, C, and D are 420 mg/L, 25 mg/L, 100 mg/L, and 380 mg/L, respectively, and the concentration threshold is 320 mg/L. In the detection process, the second antigen concentration detection may be called first to detect the four samples A, B, C, and D. As the initial concentration value of the sample A is greater than the concentration threshold of 320 mg/L, the first antigen concentration detection is automatically called to dilute the sample A by a predetermined dilution factor of 2.5, while the samples B, C, and D are still in the second antigen concentration detection. At this time, the second antigen concentration detections of the samples B, C, and D are compatible with the dilution operation in the first antigen concentration detection of the sample A. The initial concentration values of the samples B and C are sequentially detected. As the initial concentration value (380 mg/L) of the sample D is greater than the concentration threshold of 320 mg/L, the first antigen concentration detection is automatically called. At this time, the sample A is in the first antigen concentration detection, which is compatible with the first antigen concentration detection of the sample D. Concentration values of the samples A and D obtained when the detection is completed are 168 mg/L and 152 mg/L, respectively, which multiply by the predetermined dilution factor of 2.5 to finally obtain the concentrations of the samples A and D to be 420 mg/L and 380 mg/L, respectively.

The method for detecting an excessive antigen concentration according to embodiments of the present disclosure is also applicable for detecting an excessive antigen concentration of a whole blood sample, a serum sample or a pre-diluted sample.

In embodiments of the present disclosure, the target manner may be selected manually according to detection needs or be selected automatically according to a preset manner, which will not be specifically limited herein.

In embodiments of the present disclosure, the related parameter includes the test department identification, the test area identification, the sample distribution, and the concentration distribution of samples in the detection environment.

In embodiments of the present disclosure, by establishing the first functional relationship between the initial concentration value of the sample and the concentration threshold, determining the regional parameter according to the distribution of the initial concentration values of the samples, establishing the second functional relationship between the regional parameter and the initial concentration value, and determining the predetermined dilution factor according to the initial concentration value in combination with the first functional relationship and the second functional relationship, the predetermined dilution factor determined thereby is consistent with the actual detection situation, the whole detection process of the excessive antigen concentration is intelligent and automated, and the detecting effect is improved. In the detection process of the excessive antigen concentration of the sample, based on different detection environments, there may be a plurality of empirical ranges for the initial concentration value of the sample. Then, in a specific detection process of the excessive antigen concentration, an appropriate manner for calculating the predetermined dilution factor may be determined according to the parameter related to the specific detection environment.

Figure 6:
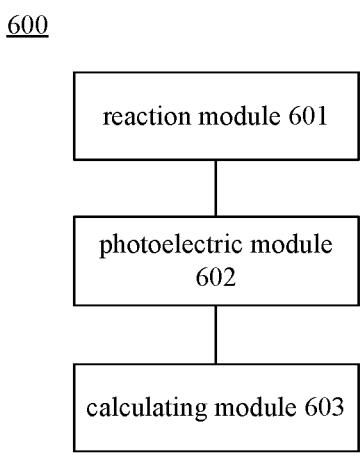
FIG. 6 is a block diagram of an apparatus for detecting an excessive antigen concentration according to an embodiment of the present disclosure.

FIG. 6 is a block diagram of an apparatus for detecting an excessive antigen concentration according to an embodiment of the present disclosure.

As illustrated in FIG. 6, the apparatus includes a reaction module 601, a photoelectric module 602, and a calculating module 603.

The reaction module 601 is configured to subject a sample containing antigens to an immune reaction.

The photoelectric module 602 is configured to obtain a photovoltage value of the sample after subjected to the immune reaction.

The calculating module 603 is configured to determine whether an antigen concentration of the sample is excessive according to the photovoltage value of the sample.

It should be illustrated that, due to the similar implementation principle, the illustrations and explanations as described hereinbefore with reference to FIGS. 1-5 for embodiments with respect to the method for detecting the excessive antigen concentration are also applicable to the embodiments with respect to the apparatus 600 for detecting the excessive antigen concentration, which will not be elaborated herein.

The division of modules in the apparatus 600 for detecting the excessive antigen concentration is for illustrative purposes only. In other embodiments, the apparatus 600 for detecting the excessive antigen concentration may be divided in other ways as required so as to complete all or part of the functions of the apparatus 600 for detecting the excessive antigen concentration.

In the present embodiments, by subjecting the sample containing antigens to the immune reaction, obtaining the photovoltage value of the sample after subjected to the immune reaction; and determining whether the antigen concentration of the sample is excessive according to the photovoltage value of the sample, the automatic detection of the excessive antigen concentration is realized. Moreover, as the detection is based on respective photovoltage values of individual samples, the detection process is effective and relatively simple, thereby effectively saving the detection cost, and improving the detection effect of the excessive antigen concentration.

In embodiments of the present disclosure, there is further provided a non-transitory computer-readable storage medium having stored therein instructions that, when executed by a processor of a mobile terminal, cause the mobile terminal to perform the method for detecting an excessive antigen concentration, including: subjecting a sample containing antigens to an immune reaction, and obtaining a photovoltage value of the sample after subjected to the immune reaction; and determining whether an antigen concentration of the sample is excessive according to the photovoltage value of the sample.

With the non-transitory computer-readable storage medium according to embodiments of the present disclosure, by subjecting the sample containing antigens to the immune reaction, obtaining the photovoltage value of the sample after subjected to the immune reaction; and determining whether the antigen concentration of the sample is excessive according to the photovoltage value of the sample, the automatic detection of the excessive antigen concentration is realized. Moreover, as the detection is based on respective photovoltage values of individual samples, the detection process is effective and relatively simple, thereby effectively saving the detection cost, and improving the detection effect of the excessive antigen concentration.

In embodiments of the present disclosure, there is further provided a computer program product having stored therein instructions that, when executed by a processor, cause the processor to perform a method for detecting an excessive antigen concentration, including: subjecting a sample containing antigens to an immune reaction, and obtaining a photovoltage value of the sample after subjected to the immune reaction; and determining whether an antigen concentration of the sample is excessive according to the photovoltage value of the sample.

With the computer program product according to embodiments of the present disclosure, by subjecting the sample containing antigens to the immune reaction, obtaining the photovoltage value of the sample after subjected to the immune reaction; and determining whether the antigen concentration of the sample is excessive according to the photovoltage value of the sample, the automatic detection of the excessive antigen concentration is realized. Moreover, as the detection is based on respective photovoltage values of individual samples, the detection process is effective and relatively simple, thereby effectively saving the detection cost, and improving the detection effect of the excessive antigen concentration.

In embodiments of the present disclosure, there is further provided a device for detecting an excessive antigen concentration, including: a processor; and a memory for storing instructions executable by the processor; wherein the processor is configured to perform the method for detecting an excessive antigen concentration as described hereinbefore.

With the device according to embodiments of the present disclosure, by subjecting the sample containing antigens to the immune reaction, obtaining the photovoltage value of the sample after subjected to the immune reaction; and determining whether the antigen concentration of the sample is excessive according to the photovoltage value of the sample, the automatic detection of the excessive antigen concentration is realized. Moreover, as the detection is based on respective photovoltage values of individual samples, the detection process is effective and relatively simple, thereby effectively saving the detection cost, and improving the detection effect of the excessive antigen concentration.

It should be noted that, terms such as "first" and "second" are used herein for purposes of description and are not intended to indicate or imply relative importance or significance. In addition, in the description of the present disclosure, the phrase of "a plurality of" means two or more than two, unless specified otherwise.

Any process or method described in a flow chart or described herein in other ways may be understood to include one or more modules, segments or portions of codes of executable instructions for achieving specific logical functions or steps in the process, and the scope of a preferred embodiment of the present disclosure includes other implementations, in which the order of execution is different from what is shown or discussed, including executing functions in a substantially simultaneous manner or in an opposite order according to the related functions. These and other aspects should be understood by those skilled in the art.

It should be understood that each part of the present disclosure may be realized by the hardware, software, firmware or their combination. In the above embodiments, a plurality of steps or methods may be realized by the software or firmware stored in the memory and executed by the appropriate instruction execution system. For example, when it is realized by the hardware, likewise in another embodiment, the steps or methods may be realized by one or a combination of the following techniques known in the art: a discrete logic circuit having a logic gate circuit for realizing a logic function of a data signal, an application-specific integrated circuit having an appropriate combination logic gate circuit, a programmable gate array (PGA), a field programmable gate array (FPGA), etc.

It can be understood by an ordinary technician that all or part of the steps in the method of the above embodiments can be implemented by instructing related hardware via programs, the program may be stored in a computer readable storage medium, and the program includes one step or combinations of the steps of the method when the program is executed.

In addition, individual functional units in the embodiments of the present disclosure may be integrated in one processing module or may be separately present in physical, or two or more units may be integrated in one module. The integrated module as described above may be achieved in the form of hardware, or may be achieved in the form of a software functional module. If the integrated module is achieved in the form of the software functional module and sold or used as a separate product, the integrated module may also be stored in a computer readable storage medium.

The above-mentioned storage medium may be a read-only memory, a magnetic disc, an optical disc, etc.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, variants and modifications can be made in the embodiments without departing from spirit, principles and scope of the present disclosure.

What is claimed is:

1. A method for detecting an excessive antigen concentration, comprising:
   subjecting a sample containing antigens to immunological reaction with an antibody specific to one of the antigens in the sample, and obtaining a photovoltage value of the sample after subjected to the immunological reaction;
   determining an initial antigen concentration value of the sample according to the photovoltage value of the sample based on a predetermined curve;
   comparing the initial antigen concentration value of the sample with a target concentration value;
   determining that the antigen concentration of the sample is excessive when the initial antigen concentration value of the sample is greater than or equal to the target concentration value, and automatically diluting the sample; and
   determining that the antigen concentration of the sample is not excessive when the initial antigen concentration value of the sample is less than the target concentration value, and determining the initial antigen concentration value as a final antigen concentration of the sample.

2. The method according to claim 1, wherein after automatically diluting the sample, the method further comprises:
   determining whether the antigen concentration of the sample after diluted is greater than or equal to the target concentration value;
   automatically diluting the sample again when the antigen concentration of the sample after diluted is greater than or equal to the target concentration value; or
   obtaining a product of the antigen concentration of the sample after diluted and a predetermined dilution factor when the antigen concentration of the sample after diluted is less than the target concentration value, and determining the product as the antigen concentration of the sample.

3. The method according to claim 1, wherein the predetermined curve is determined according to a plurality of reference samples with known antigen concentrations to identify a relation between antigen concentrations and photovoltage values;
   wherein the target concentration value is an upper limit concentration value of a linear part of the predetermined curve.

4. The method according to claim 1, wherein determining the initial antigen concentration value of the sample according to the photovoltage value of the sample based on the predetermined curve comprises:
   determining from the predetermined curve a concentration value corresponding to the photovoltage value of the sample as the initial antigen concentration value of the sample.

5. The method according to claim 1, wherein the method further comprises:
   comparing the photovoltage value of the sample with a target photovoltage value to determine whether the antigen concentration of the sample is excessive.

6. The method according to claim 1, wherein automatically diluting the sample comprises:
   automatically diluting the sample by a predetermined dilution factor,
   wherein the predetermined dilution factor is determined by a preset algorithm or based on an empirical value.

7. The method according to claim 6, further comprising:
   determining the predetermined dilution factor according to a parameter related to detection environment,
   wherein the parameter comprises: a test department identification; and a test area identification.

8. The method according to claim 6, further comprising:
   obtaining a product of the antigen concentration of the sample after diluted and the predetermined dilution factor, and determining the product as the final antigen concentration of the sample.

9. The method according to claim 6, further comprising:
establishing a first functional relationship between the initial antigen concentration value of the sample and the target concentration value;
determining a regional parameter according to distribution of the initial antigen concentration values of the samples;
establishing a second functional relationship between the regional parameter and the initial antigen concentration value; and
determining the predetermined dilution factor according to the initial antigen concentration value in combination with the first functional relationship and the second functional relationship.

* * * * *